(12) United States Patent
Lin et al.

(10) Patent No.: US 7,175,628 B2
(45) Date of Patent: *Feb. 13, 2007

(54) EXTRACTABLE FILLER FOR INSERTING MEDICINE INTO ANIMAL TISSUE

(75) Inventors: Kwan Ku Lin, Pasadena, CA (US); Philip S. Yuan, Fayetteville, NY (US)

(73) Assignee: Crosstrees Medical, Inc., Boulder, CO (US)

( * ) Notice: Subject to any disclaimer, the term of this patent is extended or adjusted under 35 U.S.C. 154(b) by 466 days.

This patent is subject to a terminal disclaimer.

(21) Appl. No.: 10/652,470

(22) Filed: Sep. 2, 2003

(65) Prior Publication Data

US 2004/0236272 A1 Nov. 25, 2004

(30) Foreign Application Priority Data

May 21, 2003 (TW) .............................. 92113771 A

(51) Int. Cl.
*A61F 5/00* (2006.01)
(52) U.S. Cl. ........................... 606/86; 604/60; 604/500
(58) Field of Classification Search ............ 604/57–64, 604/93.01, 500, 502; 606/86, 92, 93, 94; 623/17.12
See application file for complete search history.

(56) References Cited

U.S. PATENT DOCUMENTS

| | | | | |
|---|---|---|---|---|
| 5,549,679 A | * | 8/1996 | Kuslich | .................... 623/17.12 |
| 2004/0059417 A1 | * | 3/2004 | Smith et al. | ............. 623/17.11 |
| 2004/0236306 A1 | * | 11/2004 | Lin et al. | ..................... 604/500 |
| 2005/0065609 A1 | * | 3/2005 | Wardlaw | .................. 623/17.12 |
| 2005/0143688 A1 | * | 6/2005 | Lin et al. | ....................... 604/60 |

* cited by examiner

*Primary Examiner*—Kevin C. Sirmons
*Assistant Examiner*—Catherine N. Witczak
(74) *Attorney, Agent, or Firm*—Gray, Plant, Mooty, Mooty & Bennett, P.A.; Peter Forrest

(57) ABSTRACT

An extractable device is used to insert a medicinal filling into an animal tissue. The device comprises a filling member and a pasty medicine. The filling member is made of a flexible and hermetic wall and is provided with a holding portion and an injection port via which the pasty medicine is injected into the holding portion after the filling member is inserted into the animal tissue. The holding portion is provided with an opening which is releasably lashed by one end of one or more threads so as to make the opening leakproof. Upon completion of solidification of the pasty medicine in the holding portion of the filling member, other end of the thread is pulled to unlash the opening of the holding portion, thereby enabling the filling member to be extracted from the animal tissue so as to leave only the medicine in the animal tissue.

13 Claims, 13 Drawing Sheets

EXTRACTABLE FILLER FOR INSERTING MEDICINE INTO ANIMAL TISSUE

FIELD OF THE INVENTION

The present invention relates generally to an instrument which is used in the restorative operation of animal tissue disorder. More specifically this surgical instrument can be used to insert a medical material into an animal tissue such that the instrument can be separated from the medical material and drawn out of the animal tissue so as to avert the possibility of tissue rejection.

BACKGROUND OF THE INVENTION

The surgical treatment of animal tissue disorder can be generally attained by one of three methods, which include the hypodermic injection of medicine, the balloon-insertion of medicine, and the filler-insertion of medicine. For example, the U.S. Pat. Nos. 5,972,105; 6,066,154; and 6,248,110B1 disclose respectively a method for treating bone tissue disorders, such as osteoporosis and vertebral compression fractures. The method involves the use of a balloon (made by the Kyphon Crop., U.S.A.) by which the tissue is expanded to facilitate the inserting of the medicine. This balloon method is defective in design in that the medicine is apt to spread aimlessly in the tissue without boundary. Without containment, the medicine is not as effective and there is the possibility of injury to the surrounding tissues.

In order to prevent the drawbacks of the balloon method described above, the filler-insertion method is used to implant the medicine in animal tissue in such a way that the medicine is contained in the filler, and that both the medicine and the filler are implanted in the animal tissue. This filler-insertion method is often carried out in danger of the tissue rejection of the filler.

SUMMARY OF THE INVENTION

The present invention provides an extractable device for inserting a medicinal filling into an animal tissue, said device comprising:

a filling member comprising a flexible and hermetic wall and provided with a holding portion, an injection port at one end of the holding portion, and an opening at another end of the holding portion;

one or more thread, each having one end for fastening releasably said opening of said holding portion in such a manner that said opening is leakproof; and a pasty medicine to be injected into said holding portion via said injection port of said filling member in the wake of a process for inserting said filling member into the animal tissue whereby said pasty medicine solidifies in said holding portion of said filling member;

said opening of said holding portion being unfastened at the time when other end of said threads is pulled by an external force, thereby enabling said filling member to be extracted from the animal tissue so as to leave only said medicine in the animal tissue.

Preferably, said holding portion of said filling member is integrally formed by said flexible and hermetic wall into a body in the form of sac, bag, or ball.

Preferably, said pasty medicine is a mixture of a liquid and a medicinal powdered substance or medicinal granular substance.

Preferably, the device of the present invention further comprises an injection tool for injecting said pasty medicine into said holding portion via said injection port.

Preferably, said injection tool comprises a guide tube and a syringe, wherein one end of said guide tube is connected to said injection port of said filling member and another end of said guide tube is connected to said syringe in which said pasty medicine is held, so that said pasty medicine is able to be injected into said holding portion of said filling member by said syringe via said injection port and said guide tube.

Preferably, said flexible and hermetic wall is a double-layer tubular wall having one end of an inner layer thereof being provided with said injection port of said holding portion, and having another end thereof being a folded double-layer end with said opening of said holding portion, wherein said medicine is released from said filling member by pulling a free end of an outer layer of the double-layer tubular wall to retreat the folded double-layer end, after said opening of said holding portion being unfastened.

Preferably, said one or more thread is between said inner layer and said outer layer of said double-layer tubular wall.

The present invention also discloses a method for implanting a solidified medicine into an animal tissue comprising:

inserting a filling member in a hole of an animal tissue, said filling member comprising a flexible and hermetic wall and provided with a holding portion, an injection port at one end of the holding portion, and an opening at another end of the holding portion, wherein one or more thread is provided and each having one end fastening releasably said opening of said holding portion in such a manner that said opening is leakproof;

injecting a pasty medicine into said holding portion via said injection port of said filling member, whereby said pasty medicine solidifies in said holding portion of said filling member; and unfastening said opening of said holding portion by pulling other end of said threads, thereby enabling said filling member to be extracted from the animal tissue so as to leave only said solidified medicine in the animal tissue.

Preferably, the method further comprising fastening detachably an injection tool with said filling member, so that said pasty medicine is injected into said holding portion via said injection tool. More preferably, said injection tool comprises a guide tube and a syringe, wherein one end of said guide tube is connected to said injection port of said filling member and another end of said guide tube is connected to said syringe in which said pasty medicine is held, wherein said pasty medicine is injected into said holding portion of said filling member by said syringe via said injection port and said guide tube.

The flexible wall of the filling member of the present invention is hermetic and made of a biocompatible or biosynthetic material, such as rubber, elastic plastic, titanium, goat intestine, and the like. The flexible wall can be formed into an object in the form of sac, bag, ball, cylinder or rectangular column integrally or by joining separate pieces.

The filling member of the present invention may contain a ray imaging material, such as a metal wire, by which the precise position of the filling member can be easily located by a ray imaging system, such as an X-ray machine.

The features and the advantages of the present invention will be more readily understood upon a thoughtful deliberation of the following detailed description of the preferred embodiments of the present invention with reference to the accompanying drawings.

DETAILED DESCRIPTION OF THE PREFERRED EMBODIMENTS

Figure 1:
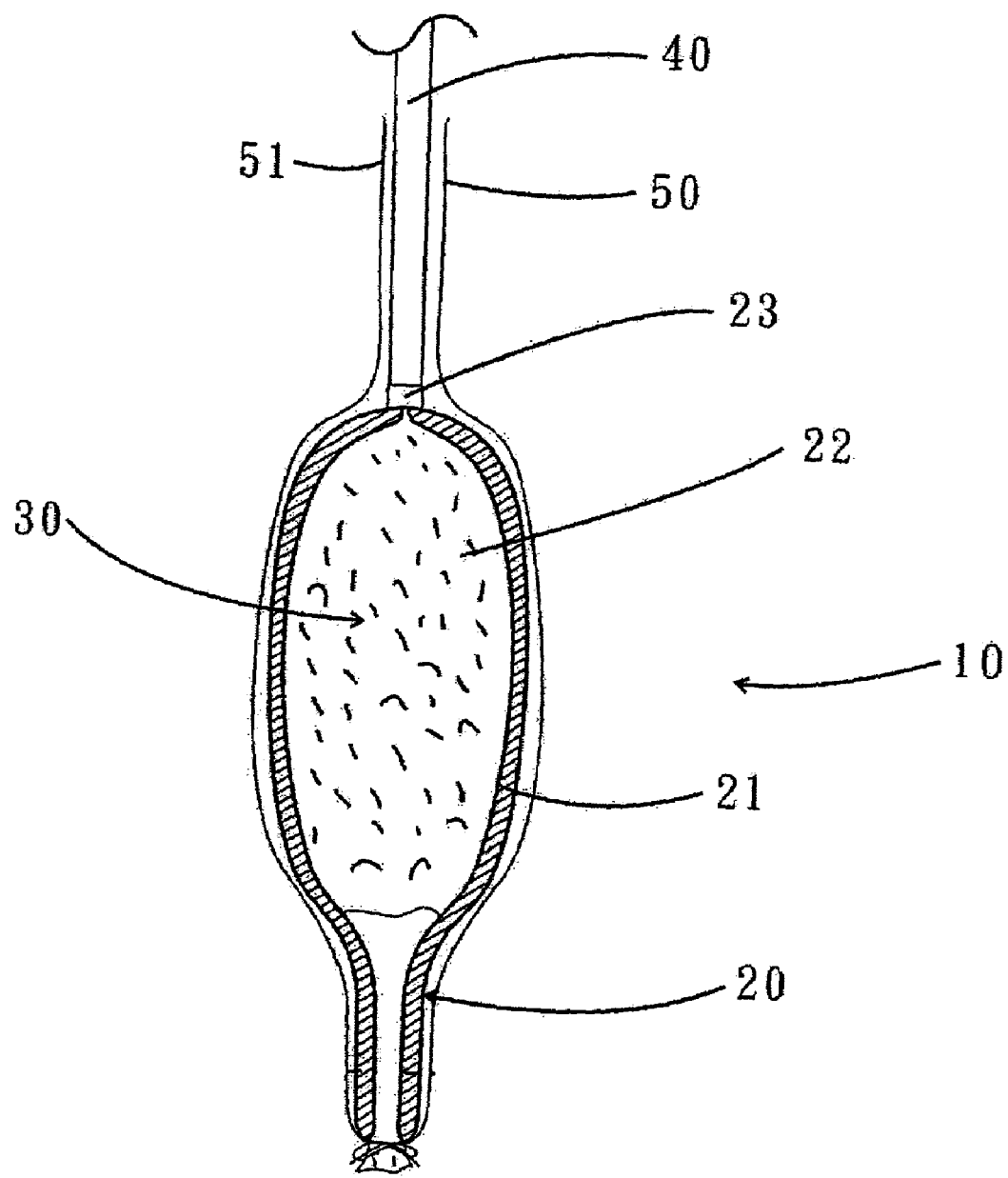
FIG. 1 shows a sectional schematic view of the present invention.

As shown in FIG. 1, an extractable filler 10 embodied in the present invention comprises a filling member 20, a pasty medicine 30, a connection tube 40, and two threads 50 and 51. The filling member 20 is formed of a flexible wall 21 and is provided with a holding portion 22 and an injection port 23. The pasty medicine 30 is injected into the holding portion 22 via the connection tube 40 and the injection port 23. The dotted line 3—3 shows a direction in which a section of the filling member 20 is taken.

Figure 2A:
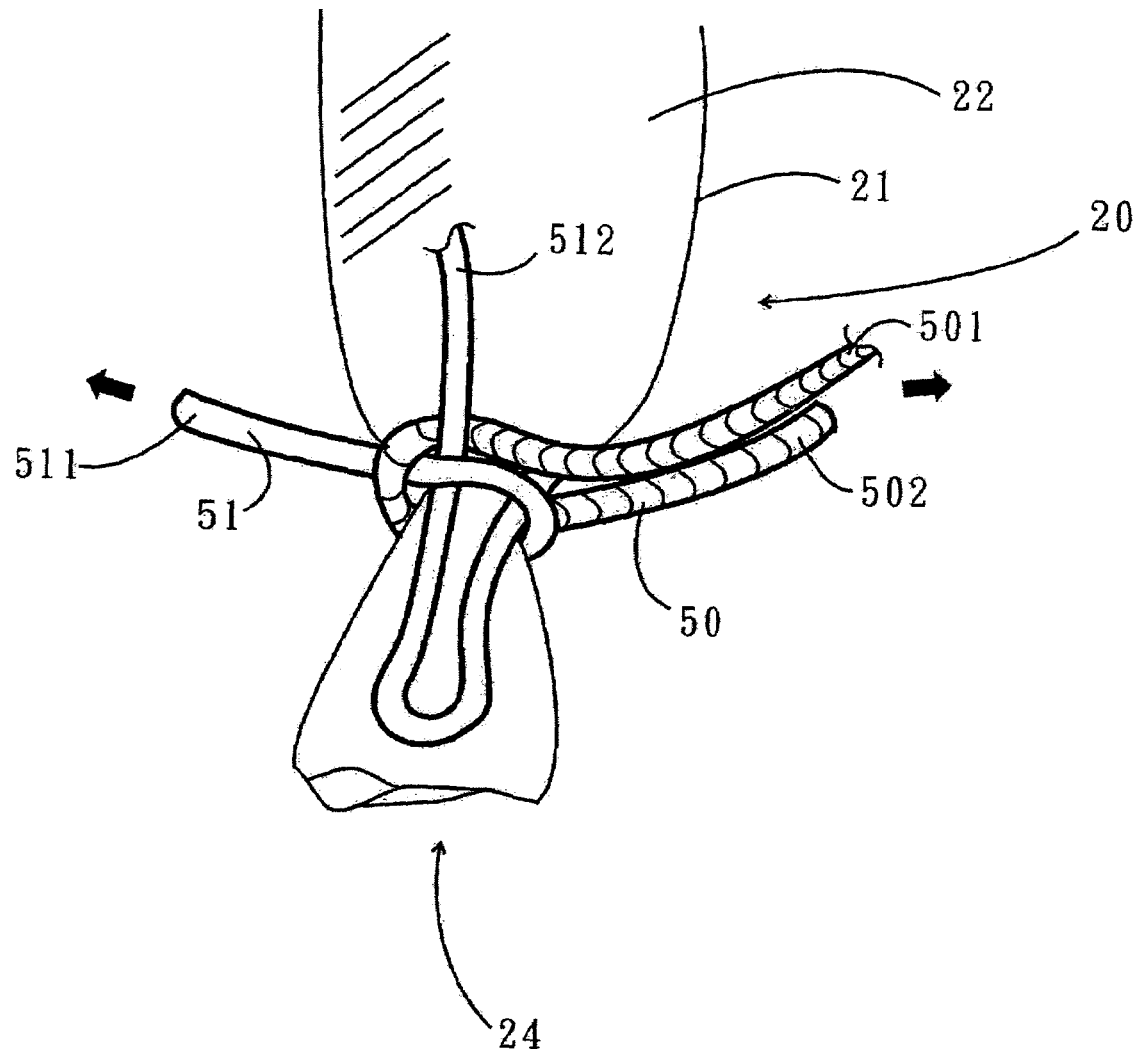
FIGS. 2a–2c are schematic views illustrating the lashing of the opening of the holding portion of the filling member of the present invention.

As shown in FIG. 2a, the holding portion 22 of the filling member 20 is integrally formed of the hermetic flexible wall 21, and is provided with an opening 24 opposite to the injection port 23 of the filling member 20. The filling member 20, for example, is an inflatable rubber balloon with an additional opening like the opening 24. The opening 24 is lashed by two threads 50 and 51. The first thread 50 has a first end 501 and a second end 502, while the second thread 51 has a first end 511 and a second end 512. The two threads 50 and 51 are in fact fastened releasably to the flexible wall 21 near the opening 24. The way by which they are fastened together is not shown in the drawing.

Figure 2B:
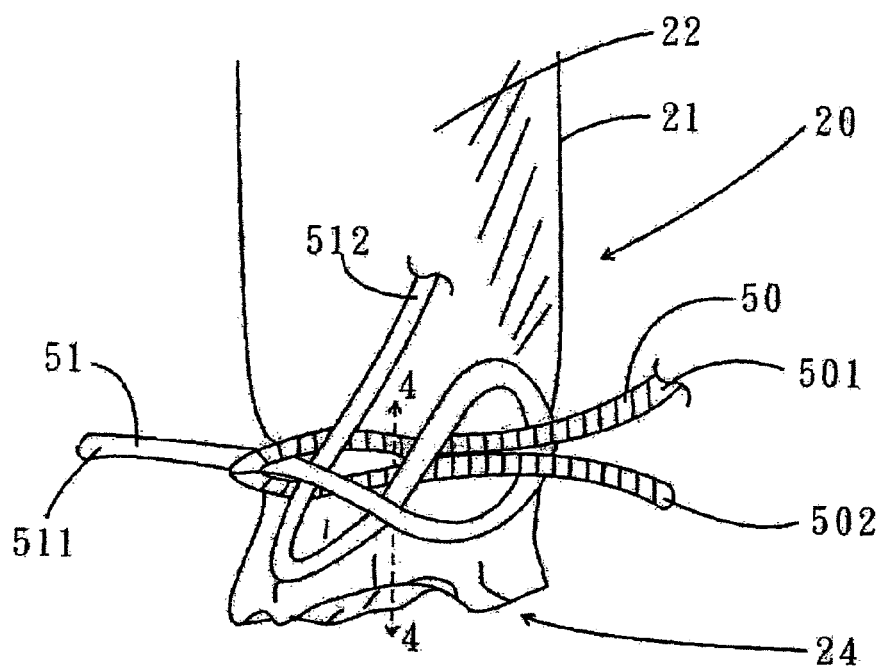

The opening 24 of the holding portion 22 of the filling member 20 is securely tied up to prevent the medicine 30 from leaking out of the holding portion 22 by means of the two threads 50 and 51 which are releasably entangled in such a manner that the first end 511 of the second thread 51 is wound around the first thread 50. Upon completion of the winding process, the flexible wall 21 surrounding the opening 24 is located in a position between the two threads 50 and 51, as indicated by a dotted line 4—4 in FIG. 2b.

Figure 2C:
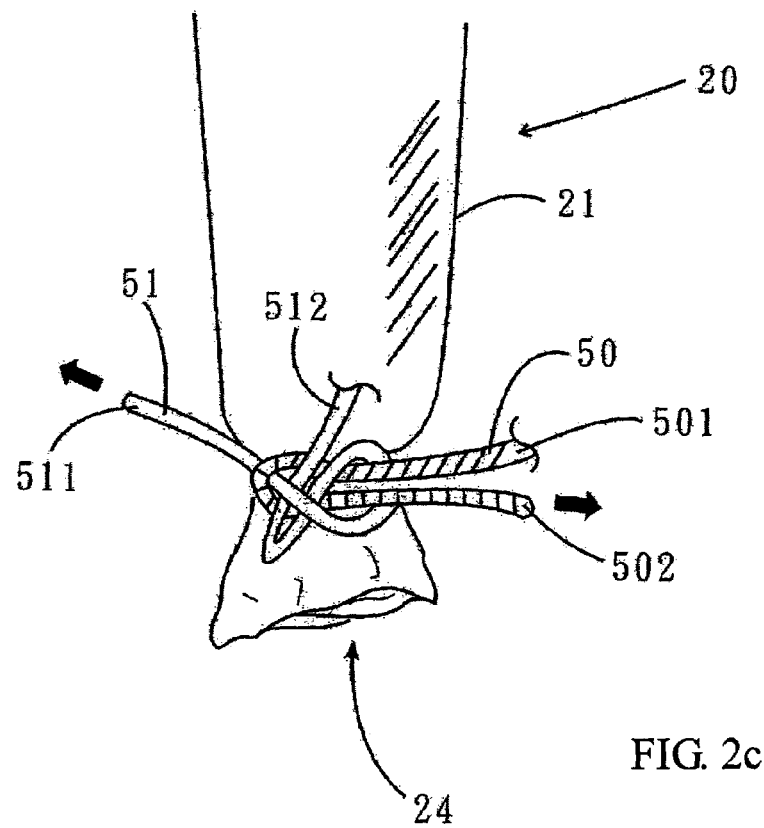

Thereafter, both ends 501 and 502 of the first thread 50, and the first end 511 of the second thread 51 are respectively pulled rightward and leftwards at the same time, as illustrated in FIG. 2c. As a result, the opening 24 of the filling member 20 is leakproof.

Figure 3A:
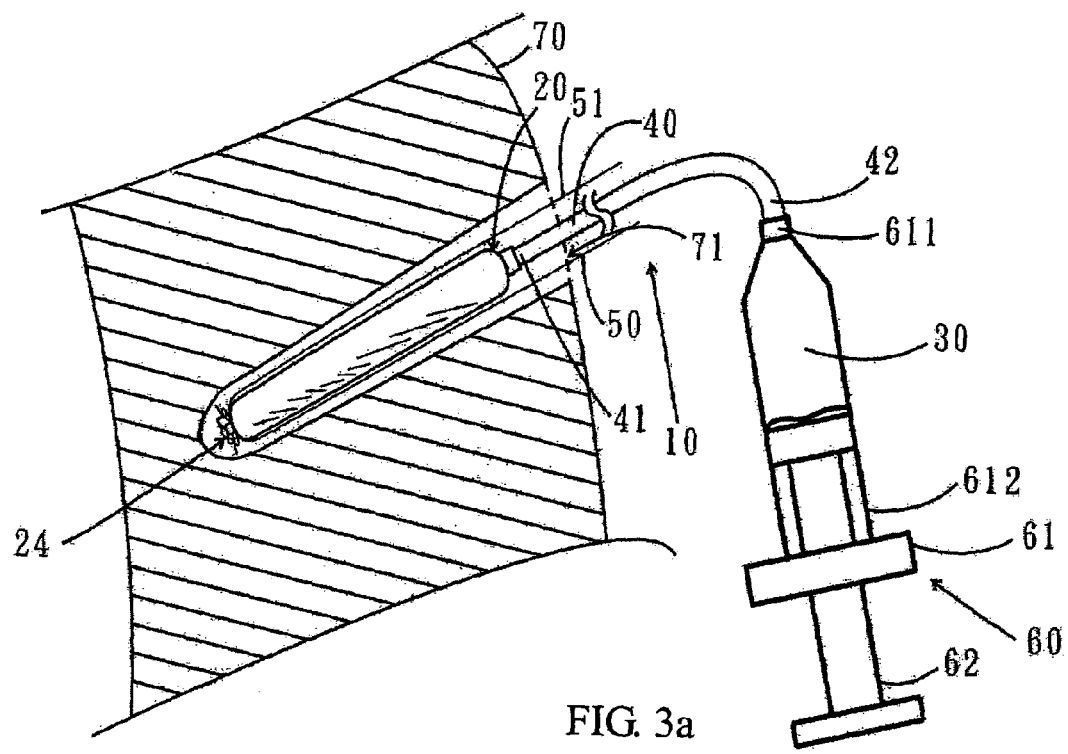
FIGS. 3a and 3b are sectional schematic view of the present invention at work.
Figure 3B:
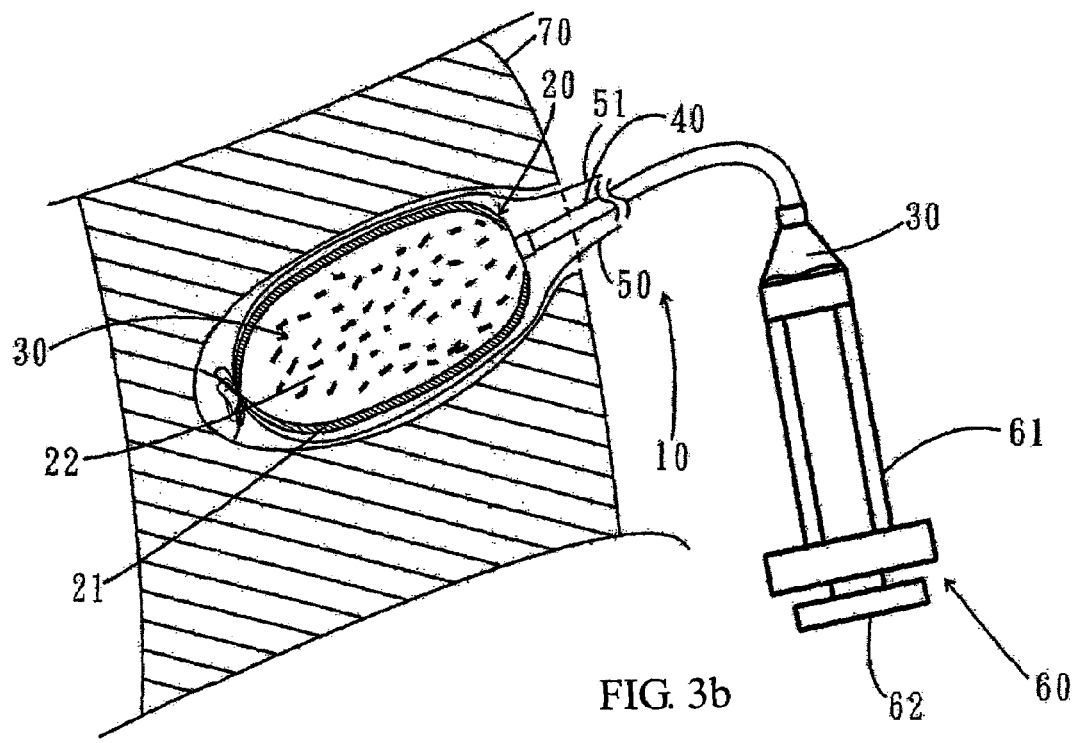

As shown in FIGS. 3a and 3b, the filling member 20 is first inserted into a blind hole 71 of an animal tissue 70. The pasty medicine 30 is then injected into the holding portion 22 of the filling member 20 by a syringe 60 in conjunction with the connection tube 40. The filling member 20 is thus inflated by the medicine 30, as shown in FIG. 3b. The connection tube 40 has one end 41 which is connected with the filling member 20, and another end 42 which is connected to one end 611 of a barrel 61 of the syringe 60. A plunger 62 is slidably inserted into another end 612 of the barrel 61 in which the pasty medicine 30 is contained.

The pasty medicine 30 is a mixture of a liquid and one or more kinds of animal tissue drugs in the form of powder, granule, or colloid. The pasty medicine 30 is capable of solidification.

Figure 4A:
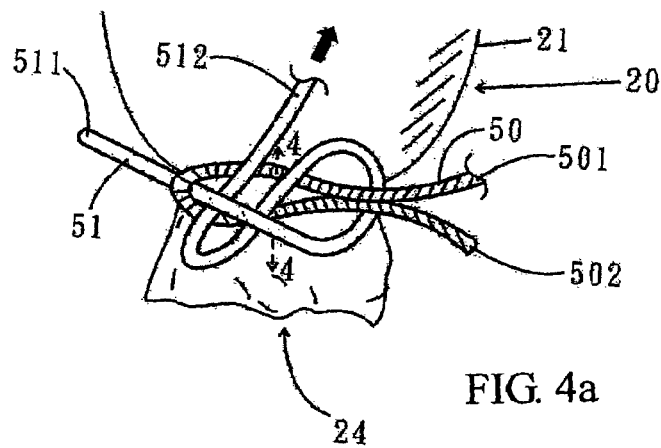
FIGS. 4a–4c are schematic views illustrating the unlashing of the opening of the holding portion of the filling member of the present invention upon completion of the injection of the medicine into the holding portion of the filling member.
Figure 4B:
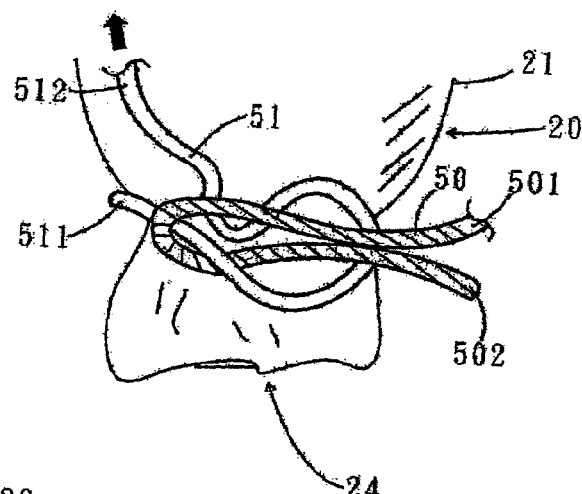
Figure 4C:
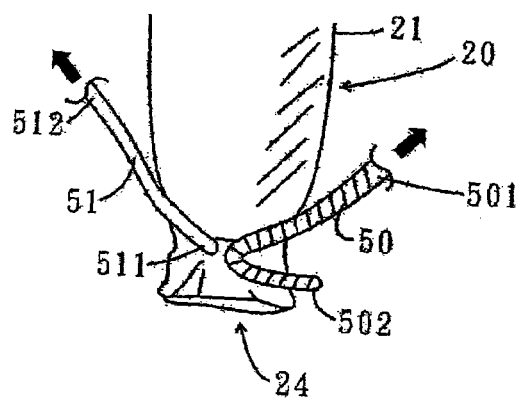

Upon completion of the solidification of the pasty medicine 30 in the blind hole 71 of the animal tissue 70, the filling member 20 must be extracted from the blind hole 71 of the animal tissue 70, so as to leave only the medicine 30 in the blind hole 71 of the animal tissue 70 to prevent the rejection of the filling member 20 by the animal tissue 70. The extraction of the filling member 20 from the blind hole 71 of the animal tissue 70 involves a first step in which the second end 512 of the second thread 51 is pulled upward as indicated by an arrow in FIG. 4a. As a result, the two threads 50 and 51 become loosened, as shown in FIG. 4b. Thereafter, the first end 501 of the first thread 50 and the second end 512 of the second thread 51 are respectively pulled in a direction away from the opening 24 of the filling member 20, as illustrated in FIG. 4c. The opening 24 is thus unfastened completely.

Figure 5A:
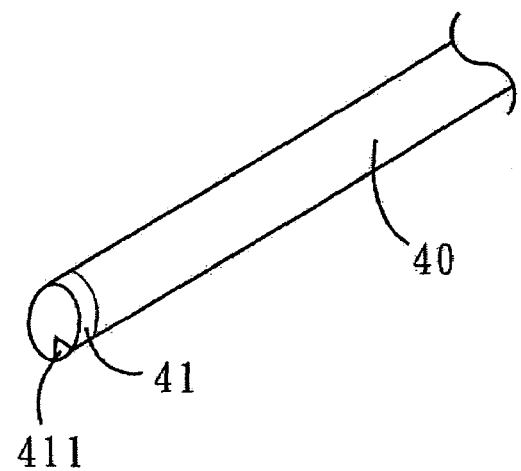
FIG. 5a shows a schematic view of the connection tube of the implantation-injection apparatus of the present invention.
Figure 5B:
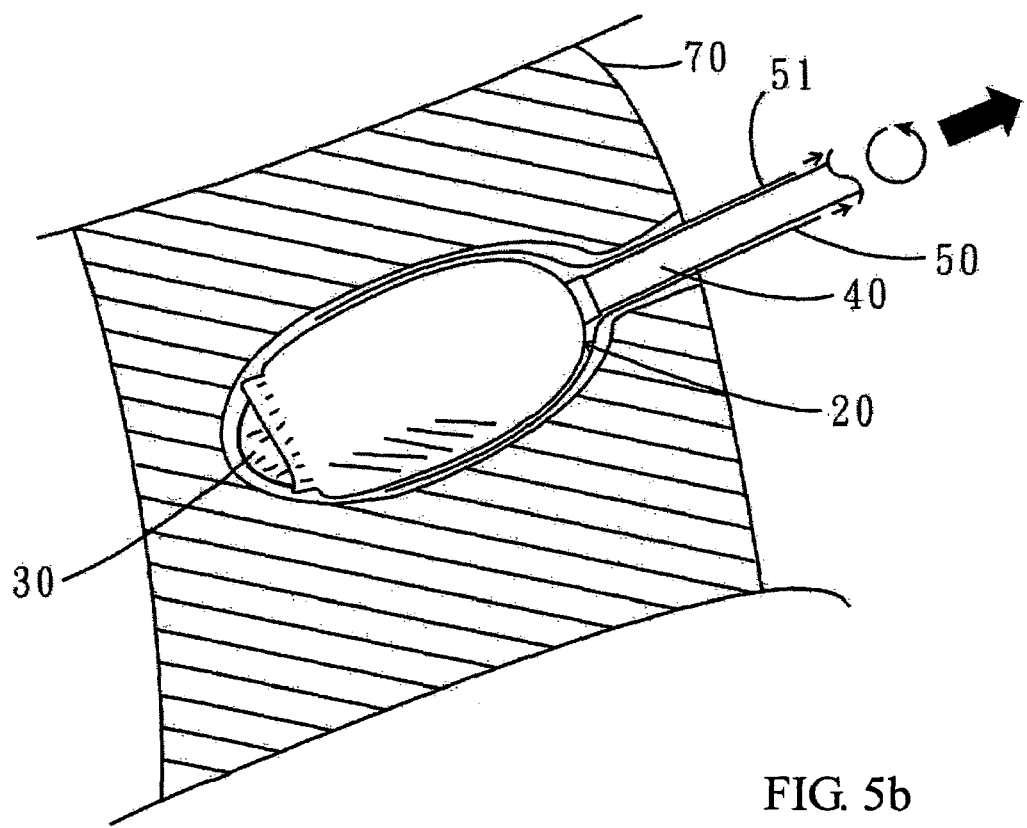
FIGS. 5b and 5c are sectional schematic views illustrating the process in which the filling member of the present invention is extracted from the animal tissue.
Figure 5C:
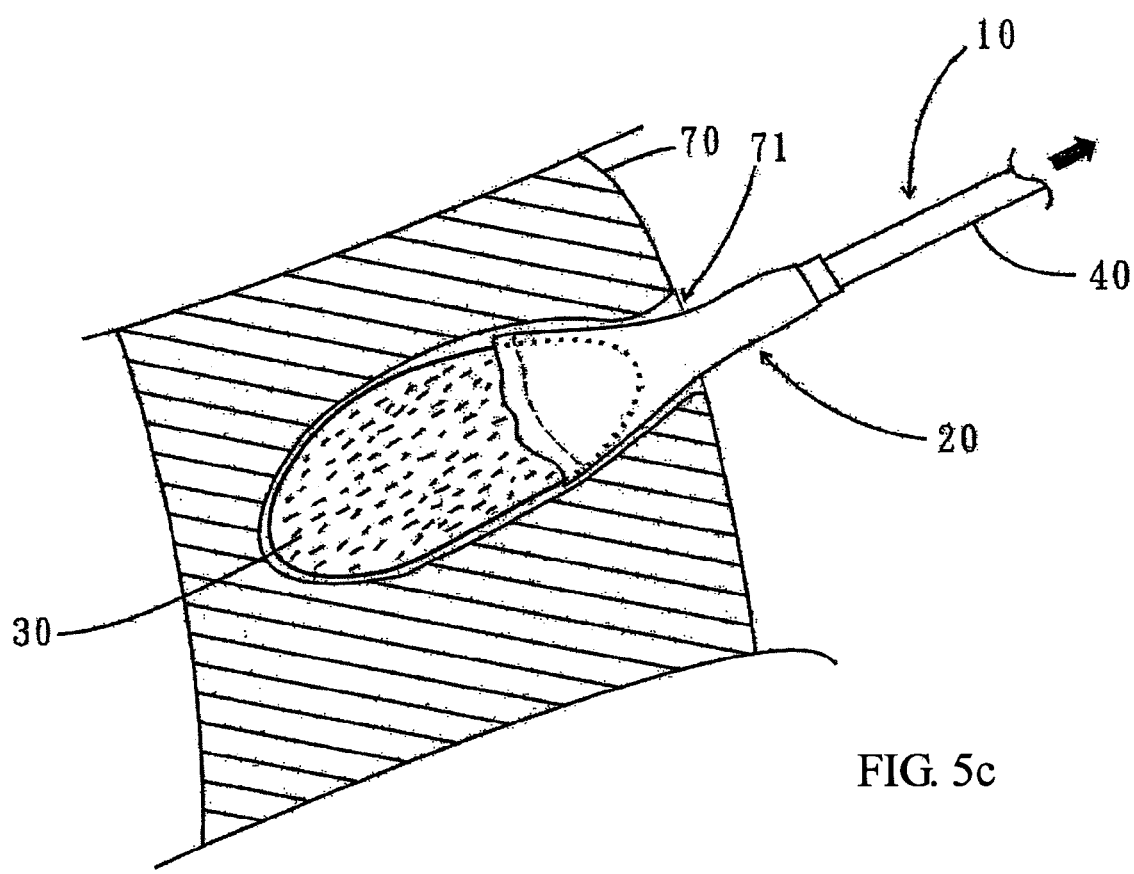

As shown in FIG. 5a, the connection tube 40 is provided in one end 41 with a pointed projection 411 inside the tube. As the connection tube 40 is slightly twisted, the solidified medicine 30 is severed by the pointed projection 411 of the connection tube 40. The filling member 20 can be drawn out of the blind hole 71 of the animal tissue 70 by the connection tube 40, as illustrated in FIG. 5b and FIG. 5c. As a result, only the medicine 30 is left in the blind hole 71 of the animal tissue.

Figure 6A:
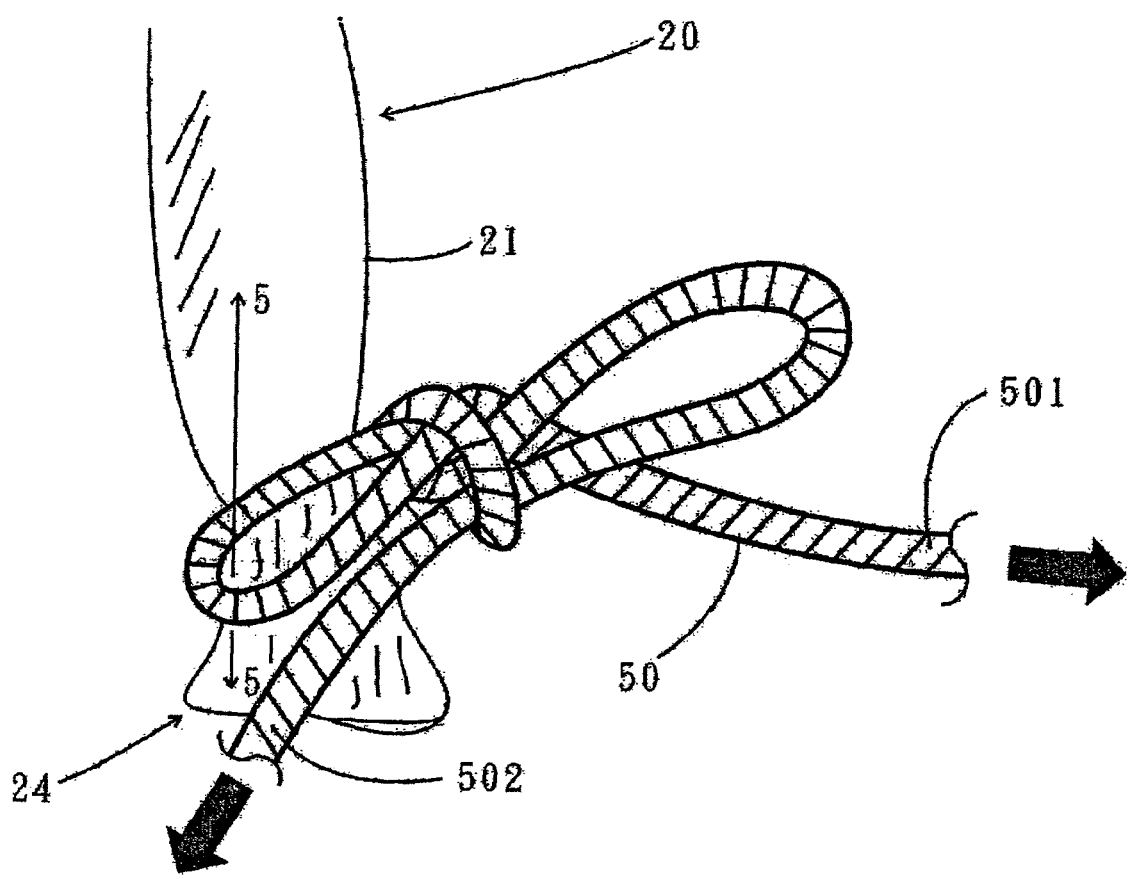
FIGS. 6a and 6b are schematic views illustrating that the opening of the holding portion of the filling member of the present invention is releasably lashed by a thread.
Figure 6B:
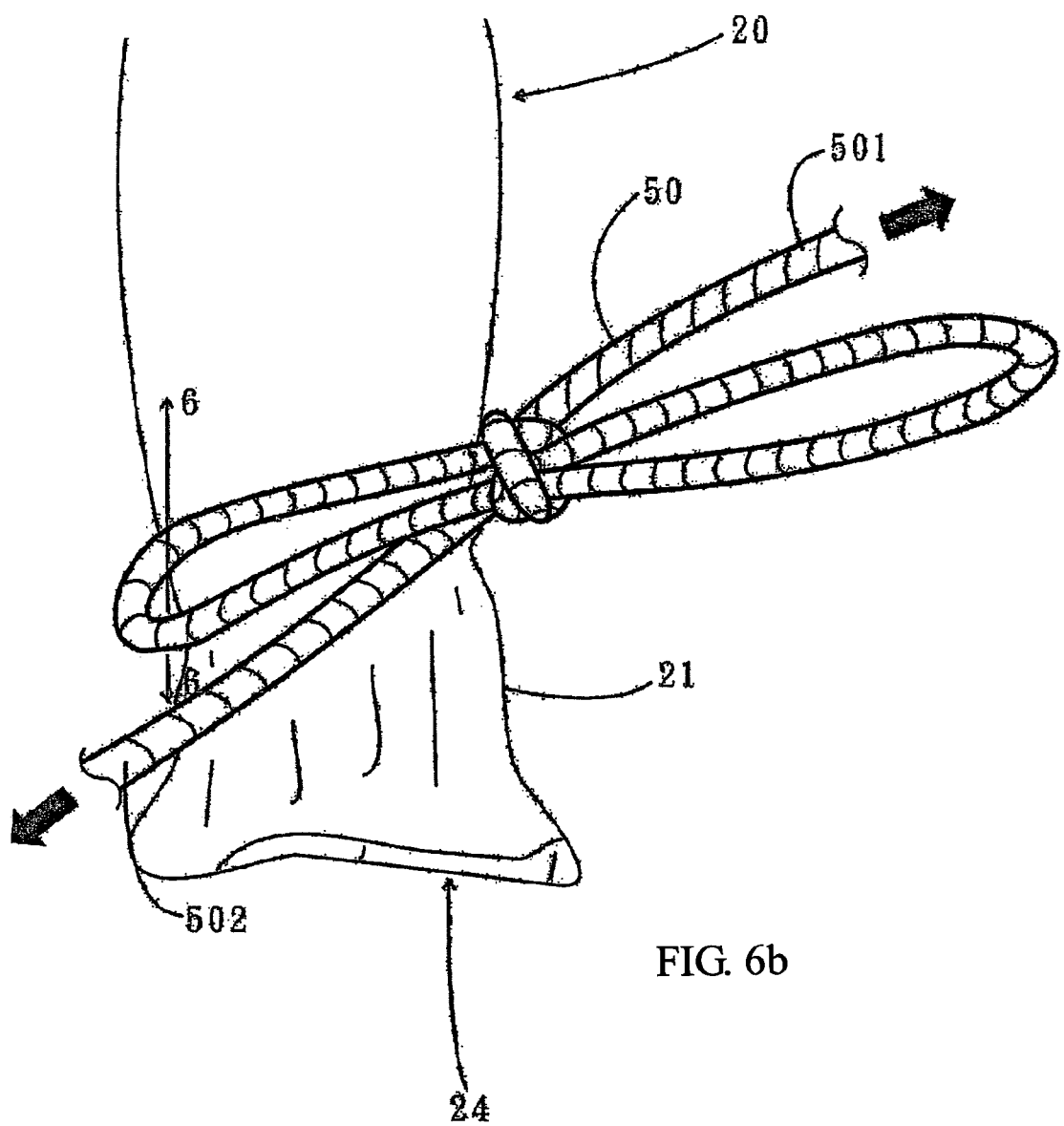

The opening 24 of the filling member 20 may be fastened by only one thread 50, as illustrated in FIGS. 6a and 6b. The thread 50 has a first end 501 and a second end 502. With the thread 50, a knot is formed to lash the opening 24 of the filling member 20 in such a manner that the flexible wall 21 of the opening 24 is surrounded by a loop as indicated by a line 5—5 in FIG. 6a. With the second end 502 of the thread 50 remaining in the stationary state, the first end 501 is pulled to fasten the opening 24. The opening 24 is unfastened by pulling the second end 502 of the thread 20, thereby resulting in separation of the filling member 20 from the thread 50.

The thread 50 can be also used to form a different knot, as shown in FIG. 6b. The flexible wall 21 of the opening 24 of the filling member 20 is surrounded by a loop as indicated by a line 6—6 in FIG. 6b. As the first end 501 of the thread 50 is pulled in a direction away from the filling member 20, the opening 24 of the filling member 20 is lashed to become leakproof. The opening 24 of the filling member 20 is unlashed to enable the filling member 20 to separate from the thread 50 by pulling the second end 502 of the thread 50.

Figure 7A:
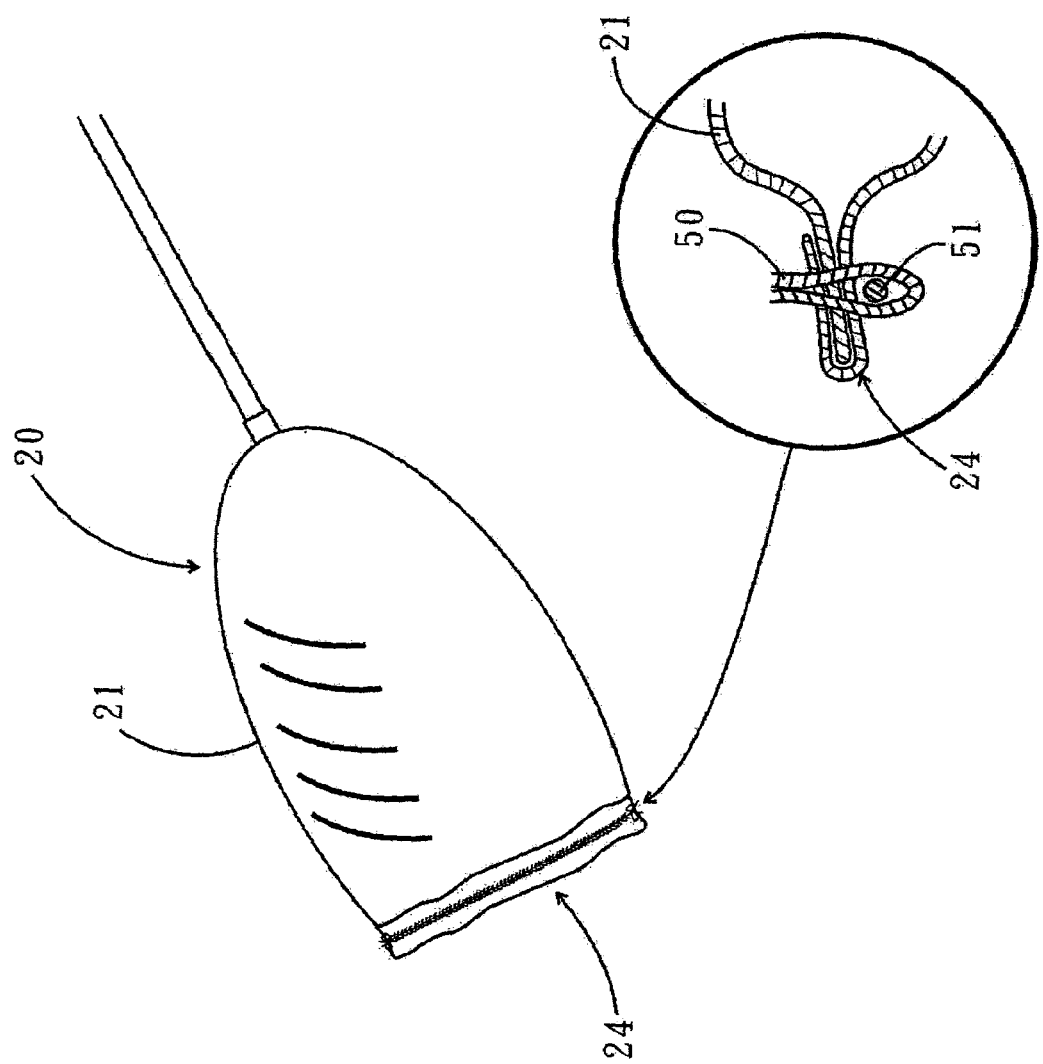
FIGS. 7a–7d are schematic views illustrating a process in which the opening of the holding portion of the filling member of the present invention is releasably lashed by two threads in conjunction with sewing.
Figure 7B:
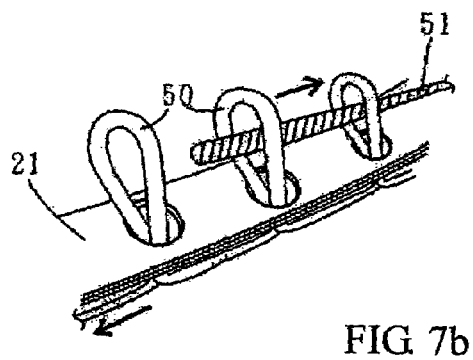
Figure 7C:
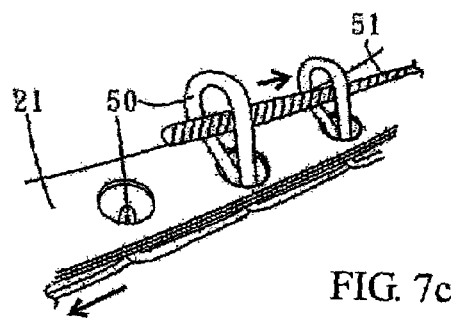
Figure 7D:
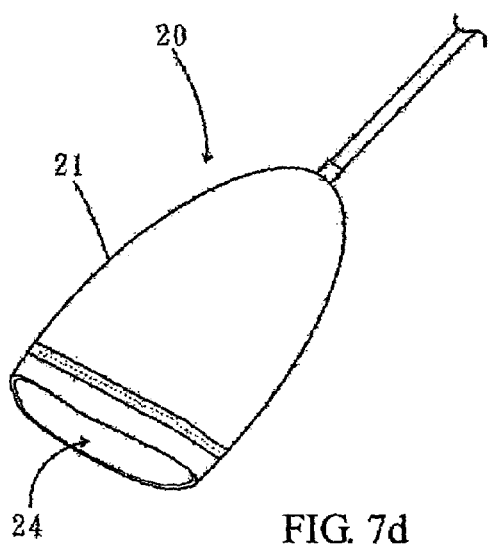

The opening 24 of the filling member 20 can be releasably fastened by sewing in conjunction with two threads 50 and 51, as illustrated in FIGS. 7a–7d. With the first thread 50, a plurality of loops are formed. These loops are joined with the flexible wall 21 of the opening 24 by sewing. The second thread 51 is put through the loops of the first thread 50. As the second thread 51 is pulled out of the loops of the first thread 50, the first thread 50 becomes separated from the flexible wall 21 of the opening 24 of the filling member 20, as illustrated in FIGS. 7b–7d. As a result, the opening 24 is unfastened. Such a fastening as described above is similar to that which is commonly used to fasten the opening of a cement or flour bag.

Figure 8A:
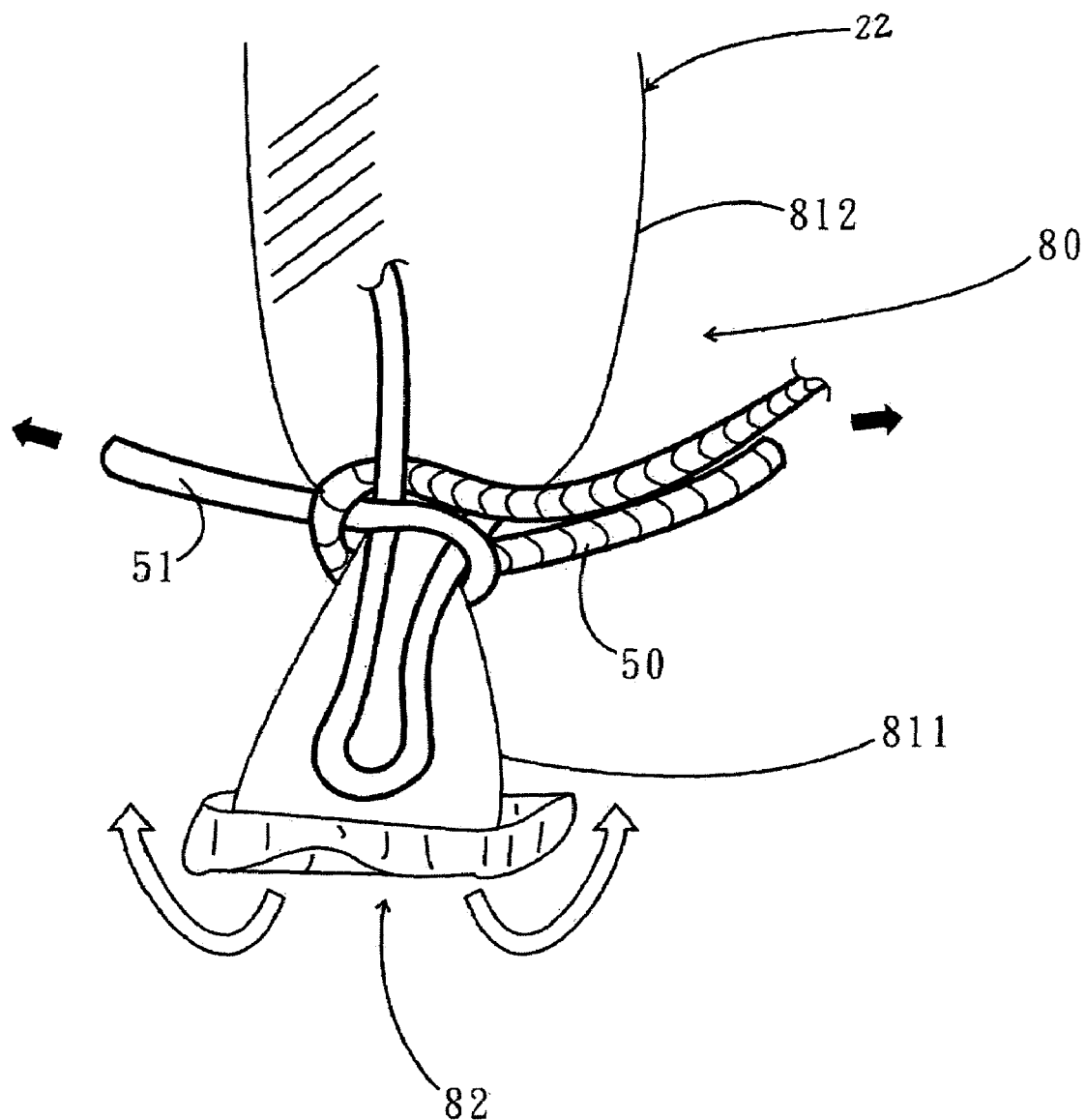
FIG. 8a is a schematic view illustrating a process in which a double-layer wall of the holding portion of the filling member of the present invention is formed.
Figure 8B:
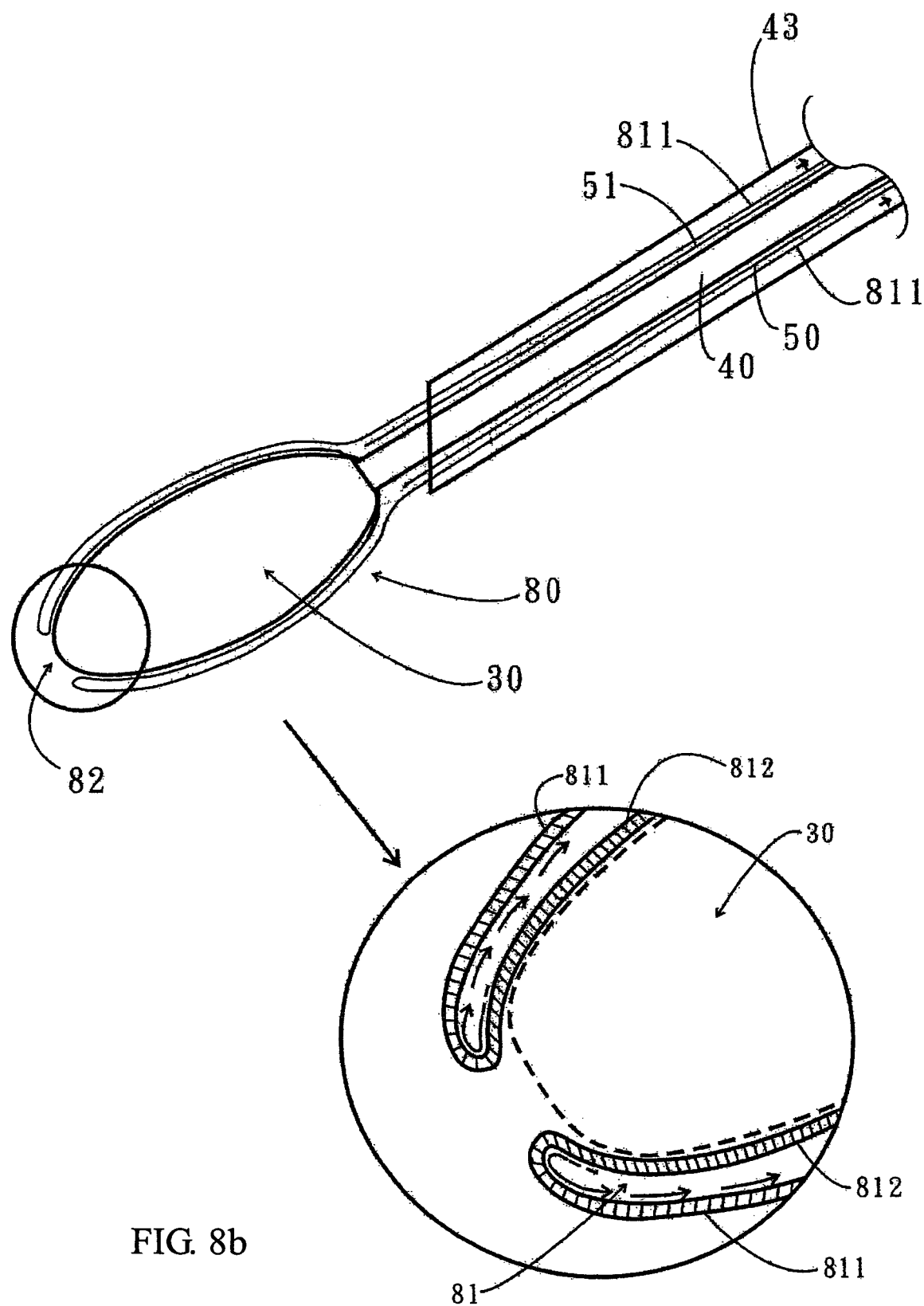
FIG. 8b illustrating a process in which the double-layer wall of the holding portion of the filling member of the present invention is retreated from the solidified medicine.

A further embodiment of the present invention is shown in FIG. 8a, and FIG. 8b, which is similar to the embodiment shown in FIGS. 1 to 2c, except that a filling member 80 is formed of a double-layer wall 81 and the first thread 51 and second thread 52 are located between an inner layer 812 and an outer layer 811 of the double-layer wall 81. As shown in FIG. 8a, a flexible and hermetic tubular wall is tied at an intermediate point thereof by the threads 50 and 51 at the beginning. The lower portion 811 of the tubular wall (will become an outer layer) is then rolled up, so that it is inside out and covering up the threads 50 and 51 and the upper portion 812 of the tubular wall (will become an inner layer). The rolled-up end of said double-layer wall 81 is provided with an opening 82 of the holding portion 22, which is lashed by the two threads 50 and 51. The opening 82 is unfastened by pulling the threads 50 and 51 the same way as shown in FIGS. 4a to 4c. As shown in FIG. 8b, the rolled-up double-layer end is retreated from the solidified medicine 30 by pulling a free end of the outer layer 811 of the double-layer wall 81, while one end of the inner layer 812 is connected to the connection tube 40 as an injection port of said holding portion 22 of the said filling member 80, whereby said solidified medicine 30 is released from said filling member 80. A working tube 43 is used to accommodate the connection tube 40, the threads 50 and 51 and the free end of the outer layer 811 of the double-layer wall 81 of the filling member 80.

The embodiments of the present invention described above are to be regarded in all respects as being illustrative and nonrestrictive. Accordingly, the present invention may be embodied in other specific forms without deviating from the spirit thereof. The present invention is therefore to be limited only the scopes of the following claims.

What is claimed is:

1. An extractable device for inserting a medicinal filling into an animal tissue, said device comprising: a filling member comprising a flexible and hermetic wall and provided with a holding portion, an injection port at one end of the holding portion, and an opening at another, releasably closable, opening end of the holding portion; one or more thread, each having one end for releasably closing said opening end of said holding portion in such a manner that said opening end is leakproof; and a pasty medicine to be injected into said holding portion via said injection port of said filling member in the wake of a process for inserting said filling member into the animal tissue whereby said pasty medicine solidifies in said holding portion of said filling member; said opening of said holding portion being reopened at the time when other end of said threads is pulled by an external force, thereby enabling said filling member to be extracted from the animal tissue so as to leave only said medicine in the animal tissue.

2. The device as defined in claim 1, wherein said holding portion of said filling member is integrally formed by said flexible and hermetic wall into a body in the form of sac, bag, or ball.

3. The device as defined in claim 1, wherein said pasty medicine is a mixture of a liquid and a medicinal powdered substance or medicinal granular substance.

4. The device as defined in claim 1, further comprising an injection tool for injecting said pasty medicine into said holding portion via said injection port.

5. The device as defined in claim 4, wherein said injection tool comprises a guide tube and a syringe, wherein one end of said guide tube is connected to said injection port of said filling member and another end of said guide tube is connected to said syringe in which said pasty medicine is held, so that said pasty medicine is able to be injected into said holding portion of said filling member by said syringe via said injection port and said guide tube.

6. The device as defined in claim 1, wherein said flexible and hermetic wall is a double-layer tubular wail having one end of an inner layer thereof being provided with said injection port of said holding portion, and having another end thereof being a folded double-layer end with said opening end of said holding portion, wherein said medicine is released from said filling member by pulling a free end of an outer layer of the double-layer tubular wall to retreat the folded double-layer end, after said opening end of said holding portion being reopened.

7. The device as defined in claim 6, wherein said one or more thread is between said inner layer and said outer layer of said double-layer tubular wall.

8. The device as defined in claim 5, wherein said flexible and hermetic wall is a double-layer tubular wall having one end of an inner layer thereof being provided with said injection port of said holding portion, and having another, releasably closable, opening end thereof being a folded double-layer, wherein said medicine is released from said filling member by pulling a free end of an outer layer of the double-layer tubular wall to retreat the folded double-layer, after said opening end of said holding portion being reopened.

9. The device as defined in claim 8, wherein said one or more thread is between said inner layer and said outer layer of said double-layer tubular wall.

10. A method for implanting a solidified medicine into an animal tissue comprising: inserting a filling member in a hole of an animal tissue, said filling member comprising a flexible and hermetic wall and provided with a holding portion, an injection port at one end of the holding portion, and an opening at another, releasably closable, opening end of the holding portion, wherein one or more thread is provided and each having one end releasably closing said opening end of said holding portion in such a manner that said opening end is leakproof; injecting a pasty medicine into said holding portion via said injection port of said filling member, whereby said pasty medicine solidifies in said holding portion of said filling member; and unfastening said opening end of said holding portion by pulling other end of said threads, thereby enabling said filling member to be extracted from the animal tissue so as to leave only said solidified medicine in the animal tissue.

11. The method as defined in claim 10, wherein said pasty medicine is a mixture of a liquid and a medicinal powdered substance or medicinal granular substance.

12. The method as defined in claim 10 further comprising fastening detachably an injection tool with said filling member, so that said pasty medicine is injected into said holding portion via said injection tool.

13. The method as defined in claim 12, wherein said injection tool comprises a guide tube and a syringe, wherein one end of said guide tube is connected to said injection port of said filling member and another end of said guide tube is connected to said syringe in which said pasty medicine is held, wherein said pasty medicine is injected into said holding portion of said filling member by said syringe via said injection port and said guide tube.

* * * * *